| United States Patent [19] | [11] | 4,202,943 |
|---|---|---|
| Suhara et al. | [45] | May 13, 1980 |

[54] RESOLUTION OF A RACEMATE

[75] Inventors: Yasuji Suhara; Hiromi Maruyama, both of Yokohama; Sayuri Itoh, Yokosuka; Kazuteru Yokose, Urayasu, all of Japan

[73] Assignee: Hoffmann-La Roche Inc., Nutley, N.J.

[21] Appl. No.: 923,842

[22] Filed: Jul. 12, 1978

Related U.S. Application Data

[63] Continuation-in-part of Ser. No. 839,525, Oct. 5, 1977, abandoned.

[30] Foreign Application Priority Data

Oct. 12, 1976 [CH] Switzerland ...................... 12875/76

[51] Int. Cl.² ............................................ C12P 13/04
[52] U.S. Cl. .................................. 435/280; 435/106
[58] Field of Search ....................... 195/2, 29; 435/280

[56] References Cited

U.S. PATENT DOCUMENTS

| 3,816,254 | 6/1974 | Chibati et al. ............................ 195/2 |
| 3,971,700 | 7/1976 | Boesten .................................... 195/2 |

OTHER PUBLICATIONS

Chemical Abstracts, vol. 82, 15278(p) 1975.
Chemical Abstracts, vol. 82, 29677(e) 1975.

*Primary Examiner*—Alvin E. Tanenholtz
*Attorney, Agent, or Firm*—Jon S. Saxe; Bernard S. Leon; George W. Johnston

[57] ABSTRACT

A process for the resolution of a racemate, namely of DL-N-benzyloxycarbonyl-2-(p-hydroxyphenyl)-glycine.

9 Claims, No Drawings

4,202,943

RESOLUTION OF A RACEMATE

RELATED APPLICATIONS

This application is a continuation-in-part application of U.S. Patent Application Serial No. 839,525, filed October 5, 1977 and now abandoned.

SUMMARY

The process provided by the present invention comprises treating DL-N-benzyloxycarbonyl-2-(p-hydroxyphenyl)-glycine with the aid of an Actinomycete belonging to the genus Streptomyces and capable of effecting the asymmetric cleavage of this racemate and subsequently isolating the resulting D-N-benzyloxycarbonyl-2-(p-hydroxyphenyl)-glycine and L-p-hydroxyphenyl-glycine from the mixture obtained.

The D-N-benzyloxycarbonyl-2-(p-hydroxyphenyl)-glycine obtainable in accordance with the present invention is a valuable intermediate for the manufacture of semisynthetic penicillins and cephalesporins. This optically active intermediate has hitherto been produced by cleavage of the corresponding racemate using a cleavage agent, the optically active isomers being obtained by fractionation of the corresponding diastereomers and treatment of the products obtained with an acid or base. Japanese Kokai No. 69039/75 discloses such a method using (+)-α-phenethylamine as the cleavage agent and a similar process is described in German Offenlegunsschrift No. 1 942 693 using quinine as the cleavage agent. In comparison with the hitherto known processes, the process provided by the present invention is significantly simpler and cheaper.

DETAILED DESCRIPTION

The microorganism used in the present process can be any Actinomycete which belongs to the genus Streptomyces and which is capable of effecting the cleavage of racemic N-benzyloxy-carbonyl-2-(p-hydroxyphenyl)-glycine. The microorganism can be used, for example, in the form of a culture broth or in the form of an extract thereof.

Preferred strains used in the present process are derived from an Actinomycete belonging to the genus Streptomyces which has been isolated from a soil sample in Seacliff Park, Adelaide City, South Australia, Australia. Also preferred are analogous strains as well as mutants and variants thereof. The aforementioned isolated Actinomycete has been deposited in Fermentation Research Institute, Agency of Industrial Science and Technology, Japan as "FERM-P No. 3666." A subculture of this deposited Actinomycete has been deposited in the microorganism collection of the United States Department of Agriculture, Northern Utilization Research and Development Division, Peoria, Ill. USA, under No. NRRL 11057.

The characteristic mycological features of the Actinomycete deposited as FERM-P No. 3666 and NRRL 11057 are as follows:

1. Morphology

The strain forms a well developed aerial mycelium (0.3–0.8×1.0–1.4 μ) with straight to slightly flexous spore-forming hyphae. Neither whorl nor spiral formation is observable. Spores, which appear in straight to slightly flexous chains with more than 50 spores per chain, are cylindrical with smooth surface.

2. Growth with various media

The following color tones are given in accordance with Color Harmony Manual, 4th Edition, 1958 (Publisher: Container Corporation of America, Chicago, USA).

(1) Saccharose nitrate agar (cultivated at 27° C.): the growth is good, colorless to brownish-grey. The aerial mycelium is greyish-white to light brownish-grey (3dc, Natural). No soluble pigment is produced.

(2) Glucose/asparagine agar (cultivated at 27° C.): The growth is good, colorless to slight yellow. The aerial mycelium is greyish-white to light brownish-grey. Slight production of a pale-yellowish, soluble pigment.

(3) Glycerine/asparagine agar (ISP-5, cultivated at 27° C.): The growth is slight olive colored (1½ ge, Light Olive Gray) to pale yellowish-brown (2 gc, Bamboo). The aerial mycelium is yellowish-white (2ba, Pearl) to light brownish-grey (3fe,Silver gray). Slight formation of a pale-yellow, soluble pigment.

(4) Inorganic salts/starch agar (ISP-4, cultivated at 27° C.): The growth is pale yellowish-brown (21g, Mustard Tan) to dark olive colored. The aerial mycelium is light brownish-grey (3dc, Natural) to light greyish-reddish-brown (5fe,Ashes). The reverse is pale yellowish-brown to dark olive colored. Slight production of a yellowish, soluble pigment.

(5) Tyrosine agar (ISP-7, cultivated at 27° C.): The growth is pale yellowish-brown (2fe, Light Mustard Tan) to dark yellowish-brown. The aerial mycelium is light grey to brownish-grey (3fe, Silver Gray). Slight formation of a yellowish, soluble pigment.

(6) Nutrient agar (Waxmans N-agar, cultivated at 27° C.): The growth is colorless to pale yellowish-brown. The aerial mycelium is greyish-white to light brownish-grey. Slight production of a brownish, soluble pigment.

(7) Yeast/malt agar (ISP-2, cultivated at 27° C.): The growth is yellowish-brown (3pi, Golden Brown). The aerial mycelium is light brownish-grey (3dc, Natural) to light greyishreddish-brown (5fe, Ashes). The reverse is yellowish-brown to dark yellowish-brown. No soluble pigment.

(8) Oatmeal agar (ISP-3, cultivated at 27° C.): The growth is light olive-grey (1½ ie, Light Olive) to pale-yellow (2ec, Oat-Meal). The aerial mycelium is light brownish-grey (3ec, Light Beige) to light greyish-reddish-brown (5fe, Ashes). The reverse is light olive-grey to pale-yellow. A yellow, soluble pigment is produced.

(9) Glucose/peptone/gelatine stab culture (cultivated at 25° C.): The growth is colorless to slight yellowish-brown. No aerial mycelium is produced, but a dark brown, soluble pigment.

(10) Skimmed milk (cultivated at 37° C.): The growth is pale-yellow, the aerial mycelium white. Brownish, soluble pigment is produced.

3. PHYSIOLOGICAL PROPERTIES (1) Optimal growth temperature: On yeast/malt agar no growth is observable at 10° C. and 45° C., whereas slight to abundant growth takes place at 25° C., 27° C., 30° C. The optimal growth temperatures lies at about 27° C.

(2) Gelatine liquefaction on glucose/peptone/gelatine agar (cultivated at 25° C.): The liquefaction is positive, but of slight to moderate intensity.

(3) Hydrolysis of the starch of inorganic salts/starch agar (cultivated at 27° C.): The hydrolysis is positive, but of moderate intensity.

(4) Coagulation and peptonization in 10% skimmed milk (cultivated at 37° C.): The peptonization is positive (moderate to strong), the coagulation positive (moderate).

(5) Melanin formation at 27° C.: No pigment on tyrosine agar (ISP-7), but brown-black pigment not only in tryptone yeast broth (ISP-1) but also on peptone/yeast/iron agar (ISP-6).

(6) Utilization of carbohydrates on Pridham-Gottlieb agar (ISP-9), (cultivated at 27° C.): Abundant growth with D-xylose, D-glucose and L-rhamnose. Good growth with L-arabinose. Slight growth with D-fructose. No growth with saccharose, inositol, raffinose and D-mannitol as well as with the controls (no addition).

The following is a compilation of the aforementioned mycological properties of the strain FERM-P No. 3666 (NRRL 11057):

FERM-P No. 3666 (NRRL 11057) is an Actinomycete belonging to the genus Streptomyces having straight to slightly flexous aerial mycelium with either whorl nor spiral formation being present. In various culture media there is produced pale-yellow to yellowish vegetative mycelium which forms light brownish-grey to light greyish-reddishbrown aerial mycelium. On some agar culture media there are found soluble pigments with yellow color tones. Melanin pigments are formed not only in tryptone/yeast broth (ISP-1) but also on peptone/yeast/iron agar (ISP-7). Hydrolysis of moderate intensity of starch and protein is observable.

Known microorganisms having properties closely related to the strain FERM-P No. 3666 (NRRL 11057) are Streptomyces xanthocidicus (International Jornal of Systematic Bacteriology, volume 22, page 372, 1972, and Jornal of Antibiotics Ser. A. volume 19, pages 195–199, 1966) and Streptomyces zaomyceticus (International Jornal of Systematic Bacteriology, volume 22, page 374, 1972 and Journal of Antibiotics, Ser. A, volume 7, pages 134–136, 1954). The following Table shows a comparison between these three microorganisms:

| Properties | FERM-P No. 3666 | Streptomyces zaomyceticus ISP-5196 | Streptomyces xanthocidicus ISP-5575 |
|---|---|---|---|
| Morphology of the Aerial mycelium | straight slightly flexous | straight slightly flexous | straight slightly flexous |
| Inorganic salt/starch agar | light brownish-grey | light brownish-grey (thin) | light brownish grey |
| Aerial mycelium | light greyish-reddish-brown | | light greyish-reddish-brown |
| Growth | pale-yellowish-brown dark olive-coloured | pale yellowish-brown yellow-brown | pale yellowish-brown |
| Soluble pigment | slightly yellow | slightly yellow | slightly yellow |
| On oatmeal agar | light brownish-grey | light brownish-grey | light brownish-grey |
| Aerial mycelium | light greyish-reddish-brown | light greyish-reddish-brown | light greyish-reddish-brown |
| Growth | light olive-grey pale-yellow | pale yellowish-brown olive-brown | pale yellow olive-grey |
| Soluble pigment | yellow | yellow | none |
| On glucose/peptone/gelatine agar | dark brown | dark brown | none or slight |
| Soluble pigment | | | |
| Melanin formation on | | | |
| ISP-1 | + | + | + |
| ISP-6 | + | + | + |
| ISP-7 | − | − | (−) |
| Reduction of nitrate | + | + | − |
| Milk coagulation | + | −−+ | − |
| Milk liquefaction | ++ | + | + |
| Gelatine liquefaction | + | + | + |
| Starch hydrolysis | + | + | + |
| Utilisation of carbohydrates | | | |
| L-arabinose | + | + | ++ |
| D-xylose | ++ | + | ++ |
| D-glucose | ++ | ++ | ++ |
| D-fructose | ± | − | ++ |
| saccharose | − | − | ++ |
| inositol | − | − | − |
| L-rhamnose | ++ | − | − |
| Raffinose | − | − | + |
| D-mannitol | − | − | − |

(++ abundant growth, + good growth, ± slight growth)

The foregoing comparisons show the similarities between the strain FERM-P No. 3666 (NRRL 11057), Streptomyces zaomyceticus and Streptomyces xanthocidicus. Ferm-P No. 3666 (NRRL 11057) differs, however, from Streptomyces xanthocidicus in its capability of reducing nitrate, in the utilization of saccharose, L-rhamnose and raffinose and in the capability of coagulating skimmed milk. FERM-P No. 3666 (NRRL 11057) differs from Streptomyces zaomyceticus in the form of the aerial mycelium on inorganic salts/starch agar and in the utilization of L-rhamnose. On the other hand, in its morphology of the aerial mycelium in its growth characteristics on glucose/peptone/gelatine medium and in its other physiological properties, the strain FERM-P No. 3666 (NRRL 11057) is more closely related to Streptomyces zaomyceticus than to Streptomyces xanthocidicus. The strain FERM-P No. 3666 (NRRL 11057) has been named Streptomyces zaomyceticus NRJA28-C-MYIa.

The DL-N-benzyloxycarbonyl-2-(p-hydroxyphenyl)-glycine used as the starting material in the process provided by the present invention can be prepared according to a number of known methods; for example, by reacting DL-p-hydroxyphenyl-glycine with benzyloxycarbonyl chloride.

The process provided by the present invention can be carried out by inoculating a culture medium containing DL-N-benzyloxycarbonyl-2-(p-hydroxyphenyl)-glycine with spores or mycleia of the Actinomycete to be used. The cultivation conditions are not particularly limited, although it is preferred to carry out the cultivation in an aqueous medium, which contains not only carbon and nitrogen sources but also inorganic salts, under aerobic conditions (which are brought about, for example, by shaking). Carbon sources are, for example, glucose, maltose and the like, nitrogen sources are, for example, polypeptones, yeast extract, meat extract, cornsteep liquor and the like and inorganic salts are, for example, phosphates or manganese, copper, zinc or iron salts and the like. The addition of special growth factors such as, for example, amino acids, nucleosides, vitamins or blood serum, is not necessary.

The temperature at which the cultivation is carried out generally lies in the range of from 20° to 40° C., preferably from 25° C. to 35° C. The cultivation is preferably carried out for 3-7 days. The cultivation is preferably carried out at a pH of 5.0-9.0.

During the asymmetric hydrolysis of the DL-N-benzyloxy-carbonyl-2-(p-hydroxyphenyl)-glycine in accordance with the present invention the pH rises; at the end of the cultivation it lies at about 8.8.

The mixture obtained after the cultivation contains D-N-benzyloxycarbonyl-2(phydroxyphenyl)-glycine and L-p- hydroxy-phenyl-glycine. These two optically active compounds can be isolated from the culture medium according to conventional methods known per se. For example, the mycelium is removed from the culture broth by centrifugation, filtration or the like, the culture solution obtained is acidified (e.g. with a mineral acid) and D-N-benzyloxycarbonyl-2-(p-hydroxyphenyl)-glycine is subsequently extracted from the acidifed solution with a water-immiscible organic solvent such as, for example, ethyl acetate, butyl acetate and the like. By removal of the solvent under reduced pressure there are obtained crude crystals of D-N-benzyloxycarbonyl-2-(phydroxyphenyl)-glycine. Optically pure D-N-benzyloxycarbonyl-2-(p-hydroxyphenyl)-glycine is obtained by purification of the crude crystals by means of usual purification methods such as recrystallization or chromatography.

The aqueous phase which contains L-p-hydroxyphenyl-glycine can be conducted through a column filled with a strong acidic cation exchange resin, the column being eluted with aqueous ammonia. The eluate is concentrated and subsequently conducted through a column filled with weak acidic cation exchange resin. By eluting the column with water there is obtained a concentrated liquid containing L-p-hydroxyphenyl-glycine which is evaporated under reduced pressure. Optically pure L-p-hydroxyphenyl-glycine is obtained as a colorless crystallizate after treatment of the residue with an organic solvent such as ethanol.

The process provided by the present invention yields optically pure D-N-benzyloxycarbonyl-2-(p-hydroxyphenyl)-glycine and L-p-hydroxyphenyl-glycine in high yields in a technically simple manner.

The following examples are illustrative but not limitative of the present invention:

EXAMPLE 1

Three 500 ml Erlenmeyer flasks are each charged with a solution (pH 7.0) of 900 mg of DL-N-benzyloxycarbonyl-2-(p-hydroxyphenyl)-glycine in 300 ml of aqueous medium containing 2% maltose, 0.5% polypeptone, 0.5% meat extract, 0.3% yeast extract, 0.3% sodium chloride, 0.1% magnesium sulfate, 80 ppm divalent manganese ions, 70 ppm divalent copper ions, 20 ppm divalent zinc ions and 10 ppm divalent iron ions, and the content of the flasks is subsequently sterilized. After the sterilization, each flask is inoculated with the strain FERM-P No. 3666 (NRRL 11057) of the microorganism Streptomyces zaomyceticus NRJA28-C-MYla. The thus-obtained culture is incubated for 5 days at 27° C. on a rotary shaking apparatus at 180 revolutions per minute.

The resulting fermentation solutions (pH 8.8) are combined and centrifuged to remove the mycelium. The supernatant phase is adjusted to pH 2.0 with concentrated aqueous hydrochloric acid and subsequently extracted three times with 300 ml of ethyl acetate each time. The organic phase is separated, dried over anhydrous sodium sulfate and evaporated under reduced pressure to give a crystalline residue. Recrystallization of the residue from chloroform containing a trace of methanol yields 340 mg of colorless needlelike crystals of D-N-benzyloxycarbonyl-2-(p-hydroxyphenyl)-glycine [yield based on the original amount of D-enantiomer: 75.5%; melting point: 157°–160° C.; $[\alpha]_D^{23} = -118°$ (c=1 in methanol)].

The aqueous phase remaining after extraction with ethyl acetate is filtered through a column filled with Dowex 50 (strong acidic cation exchange resin of sulfonated polystyrene type; H-form, 43 ml; Dow Chemicals USA). The column is washed with 150 ml of water and subsequently eluted with 0.3% aqueous ammonia. The fractions which are positive to ninhydrin are combined and concentrated to about 3 ml under reduced pressure. The concentrate is applied to a column filled with Amberlite CG-50 (weak acidic cation exchange resin of methacrylic acid type; Type I, 65 ml, mixed resin consisting of 7 parts by volume of ammonium form and 3 parts by volume of the H-form of the resin; Rohm and Haas) and the column is eluted with water. The fractions which are positive to ninhydrine are combined and evaporated under reduced pressure. Crystallization of the residue from ethanol yields 185 mg of L-p-hydroxyphenyl-glycine in the form of colorless crystals [yield based on the original amount of L-enantiomer: 74.1%; melting point: 212°–214° C.; $[\alpha]_D^{23} = +108°$ (c=1 in water).

EXAMPLE 2

A fermentation is carried out in the manner described in Example 1 with the exception that 300 mg of DL-N-benzyloxycarbonyl-2-(p-hydroxyphenyl)-glycine are used and that the fermentation time amounts to 6 days.

After the fermentation, the mycelium is centrifuged off and the supernatant phase (pH 8.8) adjusted to pH 2.0 with concentrated aqueous hydroxhloric acid. The aqueous solution is extracted twice with 70 ml of ethyl acetate each time. The organic extracts are combined, dried over aqueous sodium sulfate and concentrated under reduced pressure. The concentrate is added to a column filled with 20 ml of Wcogel C-200 (silica gel from Waco Junyaku Kogyo K.K.) and equilibrated with chloroform. The column is eluted with a mixture of chloroform and ethanol (20:1). The fractions which are positive to the Pauli reaction are combined and concentrated under reduced pressure to a crystalline residue. Recrystallization of the residue from chloroform containing a small amount of methanol yields 123 mg of D-N-benzyloxycarbonyl-2-(phydroxyphenyl)-glycine [yield: 82%; melting point: 159°–160° C.; $[\alpha]_D^{25} = -123°$ (c=1 in methanol)].

The aqueous phase remaining after extraction with ethyl acetate is worked up in the manner described in Example 1, there being obtained 67 mg of crystalline L-p-hydroxyphenyl-glycine [yield: 80.5%; melting point: 212°–215° C.; $[\alpha]_D^{26} = +109.5°$ (c=1 in water)].

We claim:

1. A process for the resolution of racemic DL-N-benzyloxycarbonyl-2-(p-hydroxyphenyl)-glycine comprising enzymatically treating said racemate with Actinomycete of the genus Streptomyces capable of effecting the asymmetric cleavage of this racemate to convert the racemte to D-N-benzyloxycarbonyl-2-(p-hydroxyphenyl)-glycine and L-p-hydroxyphenlyglycine.

2. The process of claim 1, wherein the Actinomycete is Streptomyces zaomyceticus.

3. The process of claim 2, wherein Streptomcyes zaomyceticus NRRL 11057 is used.

4. The process of claim 1 wherein the treatment is carried out in an aqueous nutrient medium which contains carbon and nitrogen sources and inorganic salts.

5. The process of claim 1 wherein the treatment is carried out under aerobic conditions.

6. The process of claim 1 wherein the treatment is carried out at a temperature of from about 20° C. to about 40° C.

7. The process of claim 6 wherein the treatment is carried out at a temperature of from about 25° C. to about 35° C.

8. The process of claim 1 wherein the treatment is carried out at a pH of 5.0–9.0.

9. The process of separating D-N-benzyloxycarbonyl-2-(p-hydroxyphenyl)-glycine from L-p-hydroxyphenylglycine in an aqueous fermentation broth comprising enzymatically treating in an aqueous medium the racemate DL-N-benzyloxycarbonyl-2-(p-hydroxyphenyl)-glycine with Actinomycete of the genus Streptomyces capable of effecting the asymmetric cleavage of said racemate, removing the resulting mycelium from the aqueous fermentation broth, acidifying the resulting broth and extracting the D-N-benzyloxycarbonyl-2-(p-hydroxyphenyl)-glycine from the acidified solution with a water immiscible organic solvent.

* * * * *